(12) United States Patent
Penthala et al.

(10) Patent No.: US 9,597,316 B2
(45) Date of Patent: *Mar. 21, 2017

(54) INDOLE COMPOUNDS FOR USE IN TREATING INFLAMMATION AND CANCER

(71) Applicants: Narsimha Reddy Penthala, Little Rock, AR (US); Peter Crooks, Little Rock, AR (US)

(72) Inventors: Narsimha Reddy Penthala, Little Rock, AR (US); Peter Crooks, Little Rock, AR (US)

(73) Assignee: BIOVENTURES LLC, Little Rock, AR (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/651,113

(22) PCT Filed: Dec. 26, 2013

(86) PCT No.: PCT/US2013/077812
§ 371 (c)(1),
(2) Date: Jun. 10, 2015

(87) PCT Pub. No.: WO2014/105957
PCT Pub. Date: Jul. 3, 2014

(65) Prior Publication Data
US 2015/0328216 A1    Nov. 19, 2015

Related U.S. Application Data

(60) Provisional application No. 61/746,884, filed on Dec. 28, 2012, provisional application No. 61/748,242, filed on Jan. 2, 2013.

(51) Int. Cl.
| | |
|---|---|
| A61K 31/404 | (2006.01) |
| A61K 45/06 | (2006.01) |
| A61K 31/515 | (2006.01) |
| C07D 403/06 | (2006.01) |

(52) U.S. Cl.
CPC .......... *A61K 31/404* (2013.01); *A61K 31/515* (2013.01); *A61K 45/06* (2013.01); *C07D 403/06* (2013.01)

(58) Field of Classification Search
CPC .... A61K 31/404; A61K 45/06; A61K 31/515; C07D 403/06
See application file for complete search history.

(56) References Cited

U.S. PATENT DOCUMENTS

| 5,484,940 A | 1/1996 | Grant et al. |
|---|---|---|
| 2004/0248950 A1 | 12/2004 | Ishizuka et al. |
| 2007/0238699 A1 | 10/2007 | Demko et al. |
| 2008/0113993 A1 | 5/2008 | De Belin et al. |
| 2009/0253656 A1 | 10/2009 | Yamazaki et al. |
| 2010/0081678 A1 | 4/2010 | Crooks et al. |
| 2011/0053941 A1 | 3/2011 | Mautino et al. |
| 2011/0077250 A1 | 3/2011 | Ryder |
| 2011/0144139 A1 | 6/2011 | Vasioukhin et al. |
| 2011/0251236 A1 | 10/2011 | Lai et al. |
| 2016/0068506 A1 | 3/2016 | Penthala et al. |
| 2016/0075689 A1* | 3/2016 | Penthala .............. C07D 403/06 514/274 |

FOREIGN PATENT DOCUMENTS

| WO | 92/04334 A1 | 3/1992 |
|---|---|---|
| WO | 2014/105957 A1 | 7/2014 |
| WO | 2014/172363 A2 | 10/2014 |
| WO | 2014/176351 A1 | 10/2014 |
| WO | 2015/153635 A1 | 10/2015 |

OTHER PUBLICATIONS

Mali et al., "An efficient green protocol for the synthesis of 2-aryl substituted benzothiazoles," Green Chemistry Letters and Reviews, 2010, pp. 209-212, vol. 3, No. 3.
Magarian et al., "New Compounds: Acrylonitrile Derivatives as Potential Antineoplastic Agents," Journal of Pharmaceutical Sciences, 1969, pp. 1166-1167, vol. 58, No. 9.
Mekouar et al., "Styrylquinoline Derivatives: A New Class of Potent HIV-1 Integrase Inhibitors That Block HIV-1 Replication in CEM Cells," J. Med. Chem., 1998, pp. 2846-2857, vol. 41.
Office Action related to U.S. Appl. No. 14/785,381 dated Feb. 8, 2016, 12 pages.
Penthala et al., "Synthesis and In Vitro Screening of Novel Heterocyclic Compounds as Potential Breast Cancer Agents," Breast Cancer-Current and Alternative Therapeutic Modalities, 2011, pp. 283-294 available on www.intechopen.com/books/breast-cancercurrent-and-alternative-therapeutic-modalities/synthesis-and-invitro-screening-of-novel-heterocycliccompounds-as-potential-breast-cancer-agents. p. 290, para 2-p. 291, para 1, Scheme 4.
Penthala et al., "Synthesis and evaluation of a series of benzothiophene acrylonitrile analogs as anticancer agents," Medchemcomm, 2013, pp. 1073-1078, vol. 4, No. 7.
International Search Report related to PCT/US14/34185, dated Nov. 7, 2014, 13 pages.
Extended European Search Report from related European Application No. 13868363.6, dated May 12, 2016; 6 pgs.
International Search Report and Written Opinion from related International Application No. PCT/US2013/077812, dated Apr. 22, 2014; 10 pgs.
International Search Report and Written Opinion from related International Application No. PCT/US2014/035169, dated Sep. 11, 2014; 7 pgs.

(Continued)

*Primary Examiner* — Alexander R Pagano
*Assistant Examiner* — Ebenezer O Sackey
(74) *Attorney, Agent, or Firm* — Polsinelli PC (57) ABSTRACT

Provided herein are compounds, comprising Formula (I) or Formula (II), and their pharmaceutically acceptable salts. Also provided are pharmaceutical compositions comprising a pharmaceutically acceptable excipient and at least one compound of Formula (I) and (II), singly or in combination with other pharmaceutically active ingredients, such as anti-inflammatory agents or anticancer agents. These compounds and pharmaceutical compositions are useful for treating inflammation or an inflammation related disorder in a subject via administration to the subject. These compounds and pharmaceutical compositions are also useful for inhibiting COX-2, for treating cancer, for reducing the size of a neoplasm, and for inhibiting tubulin polymerization in a cell.

20 Claims, 4 Drawing Sheets

(56) References Cited

OTHER PUBLICATIONS

International Search Report and Written Opinion from related International Application No. PCT/US2015/023628, dated Aug. 25, 2015; 11 pgs.

Office Action from related Canadian Patent Application No. 2,910,063, dated Jul. 6, 2016; 4 pgs.

Office Action from related U.S. Appl. No. 14/785,381, dated May 20, 2016; 11 pgs.

Haldar et al., "Synthesis of barbiturate-based methionine aminopeptidase 1 inhibitors," Bioorganic & Medicinal Chemistry Letters, 2008, pp. 2373-2376, vol. 18.

Kaur et al., "N-1 and C-3 substituted indole Schiff bases as selective COX-2 inhibitors: Synthesis and biological evaluation," Bioorganic & Medicinal Chemistry Letters, 2012, pp. 2154-2159, vol. 22.

Penthala et al., "5-((1-Aroyl-1H-indol-3-yl)methylene)-2-thioxodihydropynmidine-4,6(1H,5H)-diones as potential anticancer agents with anti-inflammatory properties," Bioorganic & Medicinal Chemistry Letters, 2013, pp. 1442-1446, vol. 23.

PubChem, Compound Summary for CID 613500, 4,5-Diphenyl-1H-1,2,3-triazole, Create Date: Mar. 28, 2005 [retrieved on May 6, 2015]; 4 pgs.

Singh et al., "Design, synthesis and anticancer activities of hybrids of indole and barbituric acids—Identification of highly promising leads," Bioorganic & Medicinal Chemistry Letters, 2009, pp. 3054-3058, vol. 19.

* cited by examiner

INDOLE COMPOUNDS FOR USE IN TREATING INFLAMMATION AND CANCER

CROSS-REFERENCE

This disclosure claims priority to U.S. provisional application Ser. No. 61/746,884 filed Dec. 28, 2012, and entitled "Methods and Compounds for Use in Treating Cancer and Inflammation," and to U.S. provisional application Ser. No. 61/748,242 filed Jan. 2, 2013, and entitled "Indole Compounds for Use in Treating Inflammation and Cancer," both of which are incorporated herein by reference in their entireties.

STATEMENT OF GOVERNMENT RIGHTS

This disclosure was made with government support under grant number U54CA119342 awarded by the National Cancer Center, and under grant number Hlo73646 awarded by the National Heart Lung and Blood Institute. The government has certain rights in the disclosure.

TECHNICAL FIELD

This disclosure generally relates to indole compounds for use in treating inflammation and cancer, including the indole compounds themselves, pharmaceutical compositions comprising the indole compounds, and methods for using the indole compounds and pharmaceutical compositions to treat inflammation, cancer, pain, and related disorders.

BACKGROUND

Molecules with both anti-cancer and anti-inflammatory properties would constitute a new approach for treating cancer. Inflammation is closely linked to cancer, and the presence of inflammation strongly correlates with the development of pre-cancerous lesions, suggesting that the presence of inflammation can induce or facilitate carcinogenesis. Various biochemical targets may be evaluated. COX-2 is the most frequently evaluated oxygenase for assessing anti-inflammatory/anticancer potential. Other targets such as NF-kB, cytokines, chemokines, fibroblast growth factor (FGF), and VEGF have also been used.

The cytotoxicity of (Z)-2-amino-5-(1-benzyl-1H-indol-3-yl)methylene-1-methyl-1H-imidazol-4(5H)-ones against human tumor cell lines (A, FIG. 1) has been reported. Related N-benzylindole analogs have displayed radiosensitizing activity (B, FIG. 1) in parallel with their cytotoxic properties. A series of structurally related N-benzylindolyl- and N-benzoyl indolylbarbituric acids (C, FIG. 1) have been reported with significant anticancer activity. A series of thiobarbituric acid analogs (D, FIG. 1) have also been described to inhibit hypoxia-inducible factor 1 (HIF-1).

Figure 1:
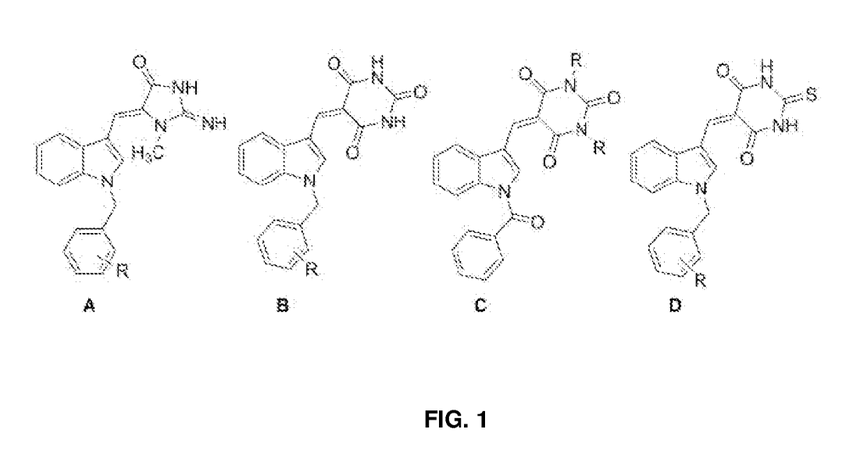
FIG. 1 shows N-benzyl and N-benzoylindole analogs (A-D).

2-Thiobarbituric acids are anticonvulsant, immunotropic, anti-inflammatory, and antineoplastic agents, as well as anti-hypnotic, and anticancer agents. More importantly, two barbituric acid analogs (FIG. 1B) have been described to possess both anticancer and anti-inflammatory properties.

SUMMARY

Generally speaking, aspects of this disclosure involve a series of molecules that possess more potent anticancer properties and anti-inflammatory properties, which may effectively treat cancers, such as melanoma, leukemia, and ovarian cancer. It is with these issues in mind, among others, that aspects of the present disclosure were conceived. Briefly, therefore, one aspect of the present disclosure encompasses compounds comprising Formula (I) or a pharmaceutically acceptable salt thereof, as shown below:

(I)

wherein:

$R^1$ is chosen from hydrogen, halogen, hydrocarbyl, and substituted hydrocarbyl;

$R^2$ is chosen from hydrocarbyl and substituted hydrocarbyl;

$X^1$ is chosen from hydrocarbyl, substituted hydrocarbyl, nitrogen, oxygen, and sulfur;

$X^2$ is chosen from hydrocarbyl, substituted hydrocarbyl, nitrogen, oxygen, and sulfur; and n is an integer from 0 to 10.

Another aspect of the present disclosure provides compounds comprising Formula (II) or a pharmaceutically acceptable salt thereof:

(II)

wherein:

R¹ is chosen from hydrogen, halogen, hydrocarbyl, and substituted hydrocarbyl;

R² is chosen from hydrocarbyl, and substituted hydrocarbyl; and n is an integer from 0 to 10.

Other aspects of the present disclosure provide pharmaceutical compositions comprising a pharmaceutically acceptable excipient and a compound of Formula (I) or Formula (II). These pharmaceutical compositions may comprise a combination of an anti-inflammatory agent or a chemotherapeutic agent with a compound of Formula (I) or Formula (II).

Also provided herein are methods for treating disorders with compounds comprising Formula (I) or Formula (II) or with pharmaceutical compositions containing compounds comprising Formula (I) or Formula (II), optionally with one or more additional pharmaceutically active ingredients, such as anti-inflammatory agents or chemotherapeutic agents. These methods may be used for treating inflammation or an inflammation related disorder in a subject, for inhibiting COX-2 in a subject, for treating cancer in a subject, for reducing the size of a neoplasm, or for inhibiting tubulin polymerization in a cell.

DETAILED DESCRIPTION (I) Indole Compounds

One aspect of the disclosure provides a compound of Formula (I):

wherein:

R¹ is chosen from hydrogen, halogen, hydrocarbyl, and substituted hydrocarbyl;

R² is chosen from hydrocarbyl, and substituted hydrocarbyl;

X¹ is chosen from hydrocarbyl, substituted hydrocarbyl, nitrogen, oxygen, and sulfur;

X² is chosen from hydrocarbyl, substituted hydrocarbyl, nitrogen, oxygen, and sulfur; and n is an integer from 0 to 10.

In one embodiment for compounds having Formula (I), n may be 0. In another embodiment, n may be between 0 and 5. In still another iteration, n may be between 5 and 10. In an additional iteration, n may be 1, 2, 3, 4, 5, 6, 7, 8, 9, or 10.

R¹ may be hydrogen. In an additional embodiment, R¹ may be halogen, including but not limited to fluorine, chlorine and bromine. In a further embodiment, R¹ may be hydrocarbyl. Suitable examples of hydrocarbyl groups include lower alkyl groups having from one to six carbon atoms. In an additional embodiment, R¹ may be substituted hydrocarbyl. Suitable examples of substituted hydrocarbyl include substituted alkyl groups having from one to six carbon atoms, such as, $\{-\}(CH_2)_nOCH_3$, $\{-\}O(CH_2)_nCH_3$, $\{-\}(CH_2)_nO(CH_2)_nCH_3$, and $\{-\}OCH_3$, where n is an integer from one to ten. In a particular embodiment, R¹ may be an acyl group having from one to six carbon atoms, for example $\{-\}COOCH_3$, $\{-\}COOC_2CH_5$, and $\{-\}COOC_3CH_7$.

R² may be hydrocarbyl. Non-limiting examples of suitable hydrocarbyls include alkyl, alkenyl, and alkynyl groups having from one to six carbon atoms. In another embodiment, R² may be substituted hydrocarbyl. Non-limiting examples of suitable substituted hydrocarbyls include alkyl, alkenyl, and alkynyl groups having from one to six carbon atoms. In a particular embodiment, R² may be phenyl or naphthyl optionally substituted with one or more F, Cl, Br, CN, CF₃, or acyl.

X¹ and X² may be independently chosen from hydrocarbyl and substituted hydrocarbyl. In another embodiment, X¹ and X² may independently be nitrogen, oxygen, or sulfur.

Examples of compounds having Formula (I) are shown in Table 1 below.

| N | R¹ | R² | X¹ | X² |
|---|---|---|---|---|
| 0, 1, 2, 3, 4, or 5 | hydrogen | C₆H₅ | carbon or nitrogen | carbon or nitrogen |
| 0, 1, 2, 3, 4, or 5 | chlorine | C₆H₅ | carbon or nitrogen | carbon or nitrogen |
| 0, 1, 2, 3, 4, or 5 | bromine | C₆H₅ | carbon or nitrogen | carbon or nitrogen |
| 0, 1, 2, 3, 4, or 5 | OCH₃ | C₆H₅ | carbon or nitrogen | carbon or nitrogen |
| 0, 1, 2, 3, 4, or 5 | hydrogen | 4-F—C₆H₄ | carbon or nitrogen | carbon or nitrogen |
| 0, 1, 2, 3, 4, or 5 | chlorine | 4-F—C₆H₄ | carbon or nitrogen | carbon or nitrogen |
| 0, 1, 2, 3, 4, or 5 | bromine | 4-F—C₆H₄ | carbon or nitrogen | carbon or nitrogen |
| 0, 1, 2, 3, 4, or 5 | OCH₃ | 4-F—C₆H₄ | carbon or nitrogen | carbon or nitrogen |
| 0, 1, 2, 3, 4, or 5 | hydrogen | 4-OCH₃—C₆H₄ | carbon or nitrogen | carbon or nitrogen |
| 0, 1, 2, 3, 4, or 5 | chlorine | 4-OCH₃—C₆H₄ | carbon or nitrogen | carbon or nitrogen |
| 0, 1, 2, 3, 4, or 5 | bromine | 4-OCH₃—C₆H₄ | carbon or nitrogen | carbon or nitrogen |
| 0, 1, 2, 3, 4, or 5 | OCH₃ | 4-OCH₃—C₆H₄ | carbon or nitrogen | carbon or nitrogen |
| 0, 1, 2, 3, 4, or 5 | hydrogen | 4-CN—C₆H₄ | carbon or nitrogen | carbon or nitrogen |
| 0, 1, 2, 3, 4, or 5 | chlorine | 4-CN—C₆H₄ | carbon or nitrogen | carbon or nitrogen |
| 0, 1, 2, 3, 4, or 5 | bromine | 4-CN—C₆H₄ | carbon or nitrogen | carbon or nitrogen |
| 0, 1, 2, 3, 4, or 5 | OCH₃ | 4-CN—C₆H₄ | carbon or nitrogen | carbon or nitrogen |
| 0, 1, 2, 3, 4, or 5 | hydrogen | 4-COOCH₃—C₆H₄ | carbon or nitrogen | carbon or nitrogen |
| 0, 1, 2, 3, 4, or 5 | chlorine | 4-COOCH₃—C₆H₄ | carbon or nitrogen | carbon or nitrogen |
| 0, 1, 2, 3, 4, or 5 | bromine | 4-COOCH₃—C₆H₄ | carbon or nitrogen | carbon or nitrogen |
| 0, 1, 2, 3, 4, or 5 | OCH₃ | 4-COOCH₃—C₆H₄ | carbon or nitrogen | carbon or nitrogen |
| 0, 1, 2, 3, 4, or 5 | hydrogen | 2-Br—C₆H₄ | carbon or nitrogen | carbon or nitrogen |
| 0, 1, 2, 3, 4, or 5 | chlorine | 2-Br—C₆H₄ | carbon or nitrogen | carbon or nitrogen |
| 0, 1, 2, 3, 4, or 5 | bromine | 2-Br—C₆H₄ | carbon or nitrogen | carbon or nitrogen |
| 0, 1, 2, 3, 4, or 5 | OCH₃ | 2-Br—C₆H₄ | carbon or nitrogen | carbon or nitrogen |

-continued

| N | $R^1$ | $R^2$ | $X^1$ | $X^2$ |
|---|---|---|---|---|
| 0, 1, 2, 3, 4, or 5 | hydrogen | 1-naphthyl | carbon or nitrogen | carbon or nitrogen |
| 0, 1, 2, 3, 4, or 5 | chlorine | 1-naphthyl | carbon or nitrogen | carbon or nitrogen |
| 0, 1, 2, 3, 4, or 5 | bromine | 1-naphthyl | carbon or nitrogen | carbon or nitrogen |
| 0, 1, 2, 3, 4, or 5 | $OCH_3$ | 1-naphthyl | carbon or nitrogen | carbon or nitrogen |
| 0, 1, 2, 3, 4, or 5 | hydrogen | 2-naphthyl | carbon or nitrogen | carbon or nitrogen |
| 0, 1, 2, 3, 4, or 5 | chlorine | 2-naphthyl | carbon or nitrogen | carbon or nitrogen |
| 0, 1, 2, 3, 4, or 5 | bromine | 2-naphthyl | carbon or nitrogen | carbon or nitrogen |
| 0, 1, 2, 3, 4, or 5 | $OCH_3$ | 2-naphthyl | carbon or nitrogen | carbon or nitrogen |
| 0, 1, 2, 3, 4, or 5 | $COOCH_3$ | $C_6H_5$ | carbon or nitrogen | carbon or nitrogen |
| 0, 1, 2, 3, 4, or 5 | $COOCH_3$ | 4-CN—$C_6H_4$ | carbon or nitrogen | carbon or nitrogen |
| 0, 1, 2, 3, 4, or 5 | $COOCH_3$ | 3-$CF_3$—$C_6H_4$ | carbon or nitrogen | carbon or nitrogen |
| 0, 1, 2, 3, 4, or 5 | CN | $C_6H_5$ | carbon or nitrogen | carbon or nitrogen |
| 0, 1, 2, 3, 4, or 5 | $CF_3$ | $C_6H_5$ | carbon or nitrogen | carbon or nitrogen |
| 0, 1, 2, 3, 4, or 5 | CN | 4-CN—$C_6H_4$ | carbon or nitrogen | carbon or nitrogen |

Another aspect of the disclosure provides compound of Formula (II):

wherein:
$R^1$ is chosen from hydrogen, halogen, hydrocarbyl, and substituted hydrocarbyl;
$R^2$ is chosen from hydrocarbyl, and substituted hydrocarbyl; and
n is an integer from 0 to 10.

In one embodiment for compounds having Formula (II), n may be 0. In another embodiment, n may be between 0 and 5. In still another iteration, n may be between 5 and 10. In an additional iteration, n may be 1, 2, 3, 4, 5, 6, 7, 8, 9, or 10.

$R^1$ may be hydrogen. In an additional embodiment, $R^1$ may be halogen, including but not limited to chlorine and bromine. In a further embodiment, $R^1$ may be hydrocarbyl. Suitable examples of hydrocarbyl groups include lower alkyl groups having from one to six carbon atoms. In an additional embodiment, $R^1$ may be substituted hydrocarbyl. Suitable examples of substituted hydrocarbyl include substituted alkyl groups having from one to six carbon atoms, such as, {—}$(CH_2)_nOCH_3$, {—}$O(CH_2)_nCH_3$, {—}$(CH_2)_nO(CH_2)_nCH_3$, and {—}$OCH_3$, where n is an integer from one to ten. In a particular embodiment, $R^1$ may be an acyl group having from one to six carbon atoms, for example {—}$COOCH_3$, {—}$COOC_2CH_5$, and {—}$COOC_3CH_7$.

$R^2$ may be hydrocarbyl. Non-limiting examples of suitable hydrocarbyls include alkyl, alkenyl, and alkynyl groups having from one to six carbon atoms. In another embodiment, $R^2$ may be substituted hydrocarbyl. Non-limiting examples of suitable substituted hydrocarbyls include alkyl, alkenyl, and alkynyl groups having from one to six carbon atoms. In a particular embodiment, $R^2$ may be phenyl or naphthyl optionally substituted with one or more F, Cl, Br, CN, $CF_3$, or acyl.

Examples of compounds having Formula (II) are shown in Table 2 below.

| n | $R^1$ | $R^2$ |
|---|---|---|
| 0 | hydrogen | $C_6H_5$ |
| 0 | chlorine | $C_6H_5$ |
| 0 | bromine | $C_6H_5$ |
| 0 | $OCH_3$ | $C_6H_5$ |
| 0 | hydrogen | 4-F—$C_6H_4$ |
| 0 | chlorine | 4-F—$C_6H_4$ |
| 0 | bromine | 4-F—$C_6H_4$ |
| 0 | $OCH_3$ | 4-F—$C_6H_4$ |
| 0 | hydrogen | 4-$OCH_3$—$C_6H_4$ |
| 0 | chlorine | 4-$OCH_3$—$C_6H_4$ |
| 0 | bromine | 4-$OCH_3$—$C_6H_4$ |
| 0 | $OCH_3$ | 4-$OCH_3$—$C_6H_4$ |
| 0 | hydrogen | 4-CN—$C_6H_4$ |
| 0 | chlorine | 4-CN—$C_6H_4$ |
| 0 | bromine | 4-CN—$C_6H_4$ |
| 0 | $OCH_3$ | 4-CN—$C_6H_4$ |
| 0 | hydrogen | 4-$COOCH_3$—$C_6H_4$ |
| 0 | chlorine | 4-$COOCH_3$—$C_6H_4$ |
| 0 | bromine | 4-$COOCH_3$—$C_6H_4$ |
| 0 | $OCH_3$ | 4-$COOCH_3$—$C_6H_4$ |
| 0 | hydrogen | 2-Br—$C_6H_4$ |
| 0 | chlorine | 2-Br—$C_6H_4$ |
| 0 | bromine | 2-Br—$C_6H_4$ |
| 0 | $OCH_3$ | 2-Br—$C_6H_4$ |
| 0 | hydrogen | 1-naphthyl |
| 0 | chlorine | 1-naphthyl |
| 0 | bromine | 1-naphthyl |
| 0 | $OCH_3$ | 1-naphthyl |
| 0 | hydrogen | 2-naphthyl |
| 0 | chlorine | 2-naphthyl |
| 0 | bromine | 2-naphthyl |
| 0 | $OCH_3$ | 2-naphthyl |
| 0 | $COOCH_3$ | $C_6H_5$ |
| 0 | $COOCH_3$ | 4-CN—$C_6H_4$ |
| 0 | $COOCH_3$ | 3-$CF_3$—$C_6H_4$ |
| 0 | CN | $C_6H_5$ |
| 0 | $CF_3$ | $C_6H_5$ |
| 0 | CN | 4-CN—$C_6H_4$ |

The compounds having Formula (I) and (II) may be provided as a pharmaceutically acceptable salt. The term "pharmaceutically acceptable salt" refers to a salt commonly used to form an alkali metal salt or addition salt of a free acid or a free base. The nature of the salt may vary, provided that it is pharmaceutically acceptable. Suitable pharmaceutically acceptable acid addition salts of compounds of the present disclosure may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic, and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, salicylic, galactaric, and galacturonic acid. Suitable pharmaceutically-acceptable base addition salts of compounds of the present disclosure include metallic salts made from aluminum, calcium, lithium, magnesium, potassium, sodium, and zinc or organic salts made from N,N'-dibenzylethylenediamine, chloroprocaine, choline, diethanolamine, ethylenediamine, meglumine (i.e., N-methylglucamine), and procaine. All of these salts may be prepared by conventional means from the corresponding compound by reacting, for example, the appropriate acid or base with the any of the compounds of the disclosure.

The compounds of Formula (I) and (II) may also be formulated as a pharmaceutical composition with one or more pharmaceutically acceptable excipients. Non-limiting examples of suitable excipients include diluents, binders, fillers, buffering agents, pH modifying agents, effervescent disintegrants, non-effervescent disintegrants, dispersing agents, stabilizers, preservatives, compaction agents, lubricants, coloring agents, and/or flavoring agents. The amount and types of excipients utilized to form the pharmaceutical composition may be selected according to known principles of pharmaceutical science.

In one embodiment, the excipient may include at least one diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lacitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may comprise a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In another embodiment, the excipient may include a filler. Suitable fillers include, but are not limited to, carbohydrates, inorganic compounds, and polyvinylpyrrolidone (PVP). By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may comprise a buffering agent. Representative examples of suitable buffering agents include, but are not limited to, MOPS, HEPES, TAPS, Bicine, Tricine, TES, PIPES, MES, Tris buffers or buffered saline salts (e.g., Tris buffered saline or phosphate buffered saline).

In various embodiments, the excipient may include a pH modifier. By way of non-limiting example, the pH modifying agent may be citric acid, sodium carbonate, or sodium bicarbonate.

In a further embodiment, the excipient may include a non-effervescent disintegrant. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth.

In another embodiment, the excipient may comprise an effervescent disintegrant. By way of non-limiting example, suitable effervescent disintegrants include sodium bicarbonate in combination with citric acid and sodium bicarbonate in combination with tartaric acid.

In another alternate embodiment, the excipient may also include a preservative. Non-limiting examples of suitable preservatives include antioxidants, such as alpha-tocopherol or ascorbate, and antimicrobials, such as parabens, chlorobutanol or phenol.

In yet another embodiment, the excipient may include a dispersion enhancer. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

In a further embodiment, the excipient may include a lubricant. Non-limiting examples of suitable lubricants include minerals such as talc or silica; and fats such as vegetable stearin, magnesium stearate, or stearic acid.

In still another embodiment, it may be desirable to provide a coloring agent. Suitable color additives include, but are not limited to, food, drug and cosmetic colors (FD&C), drug and cosmetic colors (D&C), or external drug and cosmetic colors (Ext. D&C).

In a further embodiment, the excipient may include flavoring agents. Flavoring agents may be chosen from synthetic flavor oils and flavoring aromatics and/or natural oils, extracts from plants, leaves, flowers, fruits, and combinations thereof. By way of example, these may include cinnamon oils, oil of wintergreen, peppermint oils, clover oil, hay oil, anise oil, eucalyptus, vanilla, citrus oils (such as lemon oil, orange oil, grape and grapefruit oil), and fruit essences (such as apple, peach, pear, strawberry, raspberry, cherry, plum, pineapple, and apricot). In still another embodiment, the excipient may include a sweetener. By way of non-limiting example, the sweetener may be selected from glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; stevia-derived sweeteners; chloro derivatives of sucrose such as sucralose; sugar alcohols such as sorbitol, mannitol, sylitol, and the like. Also contemplated are hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof. In still another embodiment, the excipient may include a taste-masking agent. Taste-masking materials include cellulose hydroxypropyl ethers (HPC); low-substituted hydroxypropyl ethers (L-HPC); cellulose hydroxypropyl methyl ethers (HPMC); methylcellulose polymers and mixtures thereof; polyvinyl alcohol (PVA); hydroxyethylcelluloses; carboxymethylcelluloses and salts thereof; polyvinyl alcohol and polyethylene glycol co-polymers; monoglycerides or triglycerides; polyethylene glycols; acrylic polymers; mixtures of acrylic polymers with cellulose ethers; cellulose acetate phthalate; and combinations thereof.

The weight fraction of the excipient or combination of excipients in the composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

(II) Use of Indole Compounds Either Alone or in Combination with Another Therapeutic Agent Another aspect of the present disclosure encompasses methods for treating a condition in a subject in need thereof. In general, the method comprises administering to the subject at least one compound either alone or in combination with at least one additional therapeutic agent. Without being bound by any particular theory, it is believed that certain compounds having Formula (I) and (II) inhibit cyclooxygenase-2. It is also believed that certain compounds having Formula (I) and (II) tubulin polymerization in a cell. As such, a variety of disorders or disease states may be treated with the compounds of the disclosure. Suitable disorders and diseases that may be treated include pain conditions, inflammatory disorders, and cancer.

The subject to be treated may be any subject diagnosed as having one of the indicated conditions. Moreover, the subject to be treated may be in need of treatment for the one of the conditions. That is, the subject has been diagnosed with the condition or is at risk for developing the condition, and consequently, is in need of treatment for the condition. The subject may be diagnosed with the condition using diagnostic or clinical tests that are well known. Furthermore, those of skill in the art appreciate that different diagnostic or clinical tests are used to diagnosis the different conditions or disorders. The diagnostic tools include, without limit, physical examination, patient history, screening tests, laboratory tests, molecular tests, genomic tests, imaging tools, physical tests, mental tests, and the like. Since the perception of pain may be quite subjective, tools such as the McGill Pain Questionnaire may be used to assess the quality of pain (e.g., sharp, stabbing, squeezing, etc.), and the intensity of pain may be quantified using a numerical scale that ranges from 0 to 10. Skilled diagnosticians are familiar with other indicators of pain.

In general, the subject will be a human. Without departing from the scope of the disclosure, however, other mammalian subjects may be used. Suitable mammalian subjects include; companion animals, such as cats and dogs; livestock animals, such as cows, pigs, horses, sheep, and goats; zoo animals; and research animals, such as non-human primates and rodents.

(a) Pain

In one embodiment, the compounds of Formula (I) or (II) may be used alone or in combination with at least one additional therapeutic agent for the treatment of a pain condition in a subject. If combined, the additional therapeutic agent may be an analgesic. The analgesic may be an opioid analgesic. Alternatively, the analgesic may be a non-opioid analgesic. Non-limiting examples of suitable opioid analgesics include buprenorphine, butorphanol, codeine, dihydrocodeine, dihydromorphine, etorphine, fentanyl, hydrocodone, hydromorphone, levophanol, meperidine, methadone, morphine, nalbuphine, norcodeine, normorphine, oxycodone, oxymorphone, pentazocine, and propoxyphene. In some combinations comprising an opioid analgesic, the concentration or dose of the opioid analgesic in the combination formulation may be sub-analgesic. Examples of suitable non-opioid analgesics include without limit acetylsalicylic acid, acetaminophen (paracetamol), ibuprofen, ketoprofen, indomethacin, diflunisol, naproxen, ketorolac, dichlophenac, tolmetin, sulindac, phenacetin, piroxicam, and mefamanic acid.

In general, the subject to be treated has been diagnosed as having a pain condition. As used herein, the term "pain" refers to the unpleasant sensory and emotional experience associated with actual or perceived tissue damage by a noxious stimulus. The pain may be acute or chronic pain. For example, the pain may be traumatic or inflammatory pain, which results from injury to non-neural tissue. Non-limiting examples of traumatic or inflammatory pain include arachnoiditis, arthritis, back pain, burn pain, central pain syndrome, cancer pain, headaches (including migraines, cluster, and tension headaches); head and facial pain, muscle pain (including fibromyalgia), myofascial pain syndromes; reflex sympathetic dystrophy syndrome, repetitive stress injuries, sciatica, shingles and other skin disorders, sports injuries, spinal stenosis, surgical pain, temporomandibular disorders, trauma, and/or vascular disease or injury.

Alternatively, the pain may be neuropathic pain, which results from injury to or inflammation of the central or peripheral nervous system. Neuropathic pain may occur in any part of the body and is frequently described as a hot, burning sensation, which can be devastating to the affected individual. Neuropathic pain may be acute or chronic; it may result from diseases that affect nerves (such as diabetes), from trauma, surgical procedures, arthritis, AIDS, burn injuries, cerebral or lumbar spine disease, fibromyalgia, post-eschemic pain, tumors, viral neuralgias, or, because chemotherapy drugs can affect nerves, it may be a consequence of cancer treatment. Among the many neuropathic pain conditions are diabetic neuropathy (which results from nerve damage secondary to vascular problems that occur with diabetes); reflex sympathetic dystrophy syndrome, which may follow injury; phantom limb and post-amputation pain, which may result from the surgical removal of a limb; post-herpetic neuralgia, which may occur after an outbreak of shingles; and complex regional pain syndrome or central pain syndrome, which may result from trauma to the brain or spinal cord.

Characteristic symptoms of neuropathic pain include hyperesthesia (i.e., enhanced sensitivity to a natural stimulus); allodynia (i.e., widespread tenderness or hypersensitivity to tactile stimuli); hyperalgesia (i.e., abnormal sensitivity to pain); spontaneous burning pain; and/or phantom pain (i.e., perception of pain that is non-existent). Hyperesthesia involves an unusual increased or altered sensitivity to sensory stimuli, including for example, acoustic, cerebral, gustatory, muscular, olfactory, onelric, optic, or tactile. As an example, a painful sensation from a normally painless touch stimulus. Allodynia involves an intensified, unpleasant, and painful perception of stimuli triggered by heat or by contact, which is based on a lowering of the pain threshold for these stimuli, including, for example, a non-noxious stimulus to normal skin. Hyperalgesia involves the excessive perception of a variety of stimuli, again based on a lowering of the pain threshold and thus an abnormally increased pain sense, including for example, auditory or muscular stimuli. Phantom pain involves a perception of pain in a limb that is non-existent, such as perceived pain in a limb that has been amputated, i.e. phantom limb syndrome.

(b) Inflammatory

In another embodiment, the compounds of Formula (I) or (II) may be used alone or in combination with at least one additional therapeutic agent for the treatment of inflammation in a subject. If combined, the additional therapeutic agent may be an anti-inflammatory agent. The anti-inflammatory agent may be a glucocorticoid steroid such as the naturally occurring hydrocortisone (cortisol), or synthetic glucocorticoids such as prednisone, prednisolone, methylprednisolone, dexamethasone, betamethasone, triamcinolone, beclometasone, fludrocortisones, deoxycorticosterone, alclometasone, fluocinonide, aldosterone, and derivatives thereof. Alternatively, the anti-inflammatory agent may be a non-steroidal anti-inflammatory agent (NSAID). Non-limiting examples of suitable NSAIDs include acetylsalicylic acid (aspirin), celecoxib, choline magnesium salicylate, Cox-2 inhibitors, diclofenac, diflunisal, etodolac, fenoprofen, flufenisal, flurbiprofen, ibuprofen, indomethacin, ketoprofen, ketorolac, meclofenamate, mefenamate, nabumetone, naproxen, oxaprozin, phenylbutazone, piroxicam, salsalate, sulindac, tolmetin, valdecoxib, and zomepirac.

The inflammatory disorder to be treated may be arthritis including, but not limited to, rheumatoid arthritis, spondyloarthropathies, gouty arthritis, osteoarthritis, systemic lupus erythematosus, or juvenile arthritis. In some embodiments, the inflammation may be associated with asthma, allergic rhinitis, sinus diseases, bronchitis, tuberculosis, acute pancreatitis, sepsis, infectious diseases, menstrual cramps, premature labor, tendinitis, bursitis, skin-related conditions such as psoriasis, eczema, atopic dermatitis, urticaria, dermatitis, contact dermatitis, and burns, or from post-operative inflammation including from ophthalmic surgery such as cataract surgery and refractive surgery. In a further embodiment, the inflammatory disorder may be a gastrointestinal condition such as inflammatory bowel disease, Crohn's disease, gastritis, irritable bowel syndrome, chronic cholecystitis, or ulcerative colitis. In yet another embodiment, the inflammation may be associated with diseases such as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, allergic rhinitis, respiratory distress syndrome, systemic inflammatory response syndrome (SIRS), cancer-associated inflammation, reduction of tumor-associated angiogenesis, endotoxin shock syndrome, atherosclerosis, and the like. In an alternate embodiment, the inflammatory disorder may be associated with an ophthalmic disease, such as retinitis, retinopathies, uveitis, ocular photophobia, or of acute injury to the eye tissue. In still another embodiment, the inflammation may be a pulmonary inflammation, such as that associated with viral infections or cystic fibrosis, chronic obstructive pulmonary disease, or acute respiratory distress syndrome. The inflammatory disorder may also be associated with tissue rejection, graft v. host diseases, delayed-type hypersensitivity, as well as immune-mediated and inflammatory elements of CNS diseases such as Alzheimer's, Parkinson's, multiple sclerosis, and the like.

(c) Cancer

In still another embodiment, the compounds of Formula (I) or (II) may be used alone or in combination with a chemotherapeutic agent to treat a neoplasm or a cancer. If combined, the chemotherapeutic agent may be a cytotoxic agent that affects rapidly dividing cells in general, or it may be a targeted therapeutic agent that affects the deregulated proteins of cancer cells. For example, the chemotherapeutic agent may be an alkylating agent, an anti-metabolite, an anti-tumor antibiotic, an anti-cytoskeletal agent, a topoisomerase inhibitor, an anti-hormonal agent, a targeted therapeutic agent, or a combination thereof. Non-limiting examples of alkylating agents include altretamine, benzodopa, busulfan, carboplatin, carboquone, carmustine, chlorambucil, chlornaphazine, cholophosphamide, chlorozotocin, cisplatin, cyclosphosphamide, dacarbazine (DTIC), estramustine, fotemustine, ifosfamide, improsulfan, lomustine, mechlorethamine, mechlorethamine oxide hydrochloride, melphalan, meturedopa, nimustine, novembichin, phenesterine, piposulfan, prednimustine, ranimustine, temozolomide, thiotepa, triethylenemelamine, trietylenephosphoramide, triethylenethiophosphaoramide, trimethylolomelamine, trofosfamide, uracil mustard and uredopa. Suitable anti-metabolites include, but are not limited to aminopterin, ancitabine, azacitidine, 6-azauridine, capecitabine, carmofur, cytarabine or cytosine arabinoside (Ara-C), dideoxyuridine, denopterin, doxifluridine, enocitabine, floxuridine, fludarabine, 5-fluorouracil (5-FU), gemcetabine, leucovorin (folinic acid), 6-mercaptopurine, methotrexate, pemetrexed, pteropterin, thiamiprine, trimetrexate, and thioguanine. Non-limiting examples of suitable anti-tumor antibiotics include aclacinomysin, actinomycin, adriamycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin. Non-limiting examples of suitable anti-cytoskeletal agents include colchicines, docetaxel, macromycin, paclitaxel (taxol), vinblastine, vincristine, vindesine, and vinorelbine. Suitable topoisomerase inhibitors include, but are not limited to, amsacrine, etoposide (VP-16), irinotecan, RFS 2000, teniposide, and topotecan. Non-limiting examples of suitable anti-hormonal agents such as aminoglutethimide, aromatase inhibiting 4(5)-imidazoles, bicalutamide, finasteride, flutamide, goserelin, 4-hydroxytamoxifen, keoxifene, leuprolide, LY117018, mitotane, nilutamide, onapristone, raloxifene, tamoxifen, toremifene, and trilostane. Non-limiting examples of targeted therapeutic agents include a monoclonal antibody such as alemtuzumab, bevacizumab, capecitabine, cetuximab, gemtuzumab, heregulin, rituximab, trastuzumab; a tyrosine kinase inhibitor such as imatinib mesylate; and a growth inhibitory polypeptide such as erythropoietin, interleukins (e.g., IL-1, IL-2, IL-3, IL-6), leukemia inhibitory factor, interferons, thrombopoietin, TNF-α, CD30 ligand, 4-1BB ligand, and Apo-1 ligand.

The neoplasm treated may be malignant or benign, the cancer may be primary or metastatic; the neoplasm or cancer may be early stage or late stage. Non-limiting examples of neoplasms or cancers that may be treated include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas), breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sézary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-Cell lymphoma (cutaneous), testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), unknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, and Wilms tumor (childhood).

(d) Dosage Forms

The compounds of Formula (I) and (II), whether administered alone or with any of the additional therapeutic agents detailed herein, may be administered by several means that will deliver a therapeutically effective dose. For example, the formulations may be administered orally, parenterally, by inhalation spray, rectally, intradermally, intrathecally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. Formulation of therapeutic agents is discussed in, for example, Gennaro, A. R., Remington's Pharmaceutical Sciences, Mack Publishing Co., Easton, Pa. (18th ed, 1995), and Liberman, H. A. and Lachman, L., Eds., Pharmaceutical Dosage Forms, Marcel Dekker Inc., New York, N.Y. (1980).

Preparations for oral administration generally contain inert pharmaceutically acceptable excipients in addition to the active pharmaceutical ingredient. Oral preparations may be enclosed in gelatin capsules or compressed into tablets. Common excipients used in such preparations include pharmaceutically compatible fillers/diluents such as microcrystalline cellulose, hydroxypropyl methylcellulose, starch, lactose, sucrose, glucose, mannitol, sorbitol, dibasic calcium phosphate, or calcium carbonate; binding agents such as alginic acid, carboxymethylcellulose, microcrystalline cellulose, gelatin, gum tragacanth, or polyvinylpyrrolidone; disintegrating agents such as alginic acid, cellulose, starch, or polyvinylpyrrolidone; lubricants such as calcium stearate, magnesium stearate, talc, silica, or sodium stearyl fumarate; glidants such as colloidal silicon dioxide; sweetening agents such as sucrose or saccharin; flavoring agents such as peppermint, methyl salicylate, or citrus flavoring; coloring agents; and preservatives such as antioxidants (e.g., vitamin A, vitamin C, vitamin E, or retinyl palmitate), citric acid, or sodium citrate. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil.

For topical (e.g., transdermal or transmucosal) administration, penetrants appropriate to the barrier to be permeated are generally included in the preparation. Transmucosal administration may be accomplished through the use of nasal sprays, aerosol sprays, tablets, or suppositories, and transdermal administration may be via ointments, salves, gels, patches, or creams as generally known in the art.

The amount of agent that is administered to the subject can and will vary depending upon the type of agent, the subject, the condition being treated, and the particular mode of administration. Those skilled in the art will appreciate that dosages may also be determined with guidance from Goodman & Goldman's The Pharmacological Basis of Therapeutics, Tenth Edition (2001), Appendix II, pp. 475-493, and the Physicians' Desk Reference.

Definitions

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which may be lower alkyl containing from one to eight carbon atoms in the principal chain and up to 20 carbon atoms. They may be straight or branched chain or cyclic and include methyl, ethyl, propyl, isopropyl, butyl, hexyl and the like. A "$C_2$-$C_6$ alkyl" refers to an alkyl group containing from two to six carbon atoms in the principal chain.

The term "alkenyl" as used herein describes groups which may be lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like. A methylene group is not an alkenyl group.

As used herein, the term "alkoxy" refers to an alkyl group singular bonded to oxygen, i.e., R—O. Alkyloxy groups include methoxy, ethoxy, propoxy, butoxy, and so forth. The term "$C_2$-$C_6$ alkyoxy" describes alkoxy groups having from two to six carbons in the principal chain (i.e., ethoxy, propoxy, butoxy, and the like).

The term "alkynyl" as used herein describes groups which may be lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups may be monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, exemplarly monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with exemplarly 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amide, acetal, carbamyl, carbocyclo, cyano, ester, ether, halogen, heterocyclo, hydroxy, keto, ketal, phospho, nitro, and thio.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and exemplarly 5 or 6 atoms in each ring. The heteroaromatic group exemplarly has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amide, acetal, carbamyl, carbocyclo, cyano, ester, ether, halogen, heterocyclo, hydroxy, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and exemplarly 5 or 6 atoms in each ring. The heterocyclo group exemplarly has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amide, acetal, carbamyl, carbocyclo, cyano, ester, ether, halogen, heterocyclo, hydroxy, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties exemplarly comprise 1 to 20 carbon atoms.

The "substituted hydrocarbyl" moieties described herein are hydrocarbyl moieties which are substituted with at least one atom other than carbon, including moieties in which a carbon chain atom is substituted (or replaced) with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amide, acetal, carbamyl, carbocyclo, cyano, ester, ether, halogen, heterocyclo, hydroxy, keto, ketal, phospho, nitro, and thio.

The term "treating," as used herein, refers to inhibiting or alleviating the symptoms of the disease or disorder; reversing, inhibiting, or slowing the progression of the disease or disorder; and/or preventing or delaying the onset of the disease or disorder. The term "treatment", as used herein, unless otherwise indicated, refers to the act of treating as "treating" is defined immediately above.

When introducing elements of the present disclosure or the embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the disclosure in detail, it will be apparent that modifications and variations are possible without departing from the scope of the disclosure defined in the appended claims.

EXAMPLES

The following examples illustrate various embodiments of the disclosure.

Example 1

In the preparation of compounds 3a-3z, a small sub-library of the N-aroylindole-3-carboxaldehyde precursors (1a-z) was synthesized by available literature procedures. 2-Thiobarbituric acid (2) is a strong organic acid, having a pKa of 2.1 in water. The 2-thiobarbituric acid "active" methylene group can participate in Knoevenagel condensation reactions with appropriate aldehydes or ketones that do not contain an α-hydrogen. This reaction can be performed without a base or acid catalyst.

The procedure involves refluxing the appropriate indole-3-carboxaldehyde with 2-thiobarbituric acid in an polar protic solvent, such an alcohol. In a particular embodiment, the alcohol was methanol, and the reaction temperature was about 65° C. The reaction mixture was refluxed to completion, which was typically about 4 hours, for example about 6 hours. The reaction afforded the desired 5-((1-aroyl-1H-indol-3-yl)methylene)-2-thioxodihydropyrimidine-4,6-(1H, 5H)-dione (Table 3). Yields obtained were in the range of about 89% to about 95%. Purities were generally at least about 95%, such as at least about 99%. All the synthesized compounds were fully characterized by $^1$H and $^{13}$C-NMR spectroscopy.

TABLE 3

List of N-aroyl indolethiooxodihydropyrimidine-4,6(1H,5H)-dione analogs synthesized (3a-z)

| Compound Number | $R^1$ | $R^2$ |
|---|---|---|
| 3a | H | $C_6H_5$ |
| 3b | Cl | $C_6H_5$ |
| 3c | Br | $C_6H_5$ |
| 3d | $OCH_3$ | $C_6H_5$ |
| 3e | H | 4-F—$C_6H_4$ |
| 3f | Cl | 4-F—$C_6H_4$ |
| 3g | Br | 4-F—$C_6H_4$ |
| 3h | H | 4-$OCH_3$—$C_6H_4$ |
| 3i | Cl | 4-$OCH_3$—$C_6H_4$ |
| 3j | Br | 4-$OCH_3$—$C_6H_4$ |
| 3k | $OCH_3$ | 4-$OCH_3$—$C_6H_4$ |
| 3l | H | 4-CN—$C_6H_4$ |
| 3m | Cl | 4-CN—$C_6H_4$ |
| 3n | H | 4-$COOCH_3$—$C_6H_4$ |
| 3o | Cl | 4-$COOCH_3$—$C_6H_4$ |
| 3p | H | 2-Br—$C_6H_4$ |
| 3q | Cl | 2-Br—$C_6H_4$ |
| 3r | Br | 2-Br—$C_6H_4$ |
| 3s | $OCH_3$ | 2-Br—$C_6H_4$ |
| 3t | H | 1-naphthyl |
| 3u | Cl | 1-naphthyl |
| 3v | Br | 1-naphthyl |
| 3w | $OCH_3$ | 1-naphthyl |
| 3x | H | 2-naphthyl |
| 3y | Cl | 2-naphthyl |
| 3z | $OCH_3$ | 2-naphthyl |

Example 2

The preliminary evaluation of compounds 3a-z was carried out at a single dose of 10 μM, against a panel of 60 human tumor cell lines, according to the procedure described by Rubinstein et al., Natl. Cancer. Inst., 1990, 82, 1112, which is incorporated herein by reference in its entirety. The human tumor cell line panel included leukemia, non-small cell lung, colon, central nervous system (CNS), melanoma, ovarian, renal, prostate, and breast cancer cell lines. From the single dose-response studies, analogs 3k, 3s, 3t, and 3w showed ≥60% growth inhibition in more than eight of the 60 cancer cell lines.

Compounds 3k, 3s, 3t, and 3w were subsequently evaluated in five dose-response studies for their in vitro cytotoxic effects on growth parameters against each of the 60 human tumor cell lines. Dose-response curves were created by plotting cytotoxic effect against the $\log_{10}$ of the drug concentration for each cell line. Cytotoxic effects of each compound were determined as $GI_{50}$ and $LC_{50}$ values, which represent the molar drug concentration for causing 50% growth inhibition, and the concentration that kills 50% of the cells, respectively. The growth inhibition results are presented in Table 4.

TABLE 4

Growth inhibition concentration ($GI_{50}$) and cytotoxicity ($LC_{50}$) data of Compounds 3k and 3s on various human tumor cell lines.

| Panel/Cell line | 3k $GI_{50}$ (µM) | 3k $LC_{50}$ (µM) | 3s $GI_{50}$ (µM) | 3s $LC_{50}$ (µM) | 3t $GI_{50}$ (µM) | 3t $LC_{50}$ (µM) | 3w $GI_{50}$ (µM) | 3w $LC_{50}$ (µM) |
|---|---|---|---|---|---|---|---|---|
| Leukemia | | | | | | | | |
| CCRF-CEM | 2.23 | >50 | 4.00 | >100 | 3.35 | >100 | 3.31 | >100 |
| HL-60(TB) | 3.91 | >50.0 | 3.24 | >100 | 3.36 | >100 | 3.47 | >100 |
| K-562 | 2.55 | >50.0 | 3.80 | >100 | 3.71 | >100 | 3.52 | >100 |
| MOLT-4 | — | — | — | — | 3.49 | 79.0 | 3.95 | >100 |
| SR | 1.45 | 39.4 | 2.55 | >100 | 2.74 | 92.3 | 3.32 | >100 |
| Non-Small Cell Lung Cancer | | | | | | | | |
| HOP-62 | 3.12 | >50.0 | 3.59 | 64.3 | 1.30 | 44.8 | 1.09 | >100 |
| Colon Cancer | | | | | | | | |
| HCT-116 | 1.95 | >50.0 | 3.76 | >100 | 2.90 | >100 | 3.35 | >100 |
| HCT-15 | 1.80 | >50.0 | 3.83 | 89.9 | 3.60 | >100 | 3.10 | >100 |
| KM-12 | 1.99 | >50.0 | 3.87 | 51.9 | — | — | — | — |
| CNS Cancer | | | | | | | | |
| SF-268 | 2.65 | >50.0 | 3.86 | 52.2 | — | — | — | — |
| SF-539 | 2.56 | >50.0 | 3.00 | 57.8 | 3.68 | 58.6 | 2.30 | >100 |
| U251 | 1.93 | >50.0 | 3.09 | 42.1 | 3.58 | 50.7 | 3.23 | >100 |
| Melanoma | | | | | | | | |
| LOX IMVI | 1.86 | >50.0 | 2.92 | 47.9 | 3.59 | 55.6 | 3.80 | >100 |
| M14 | 2.03 | >50.0 | 3.52 | >100 | 3.22 | >100 | 1.91 | >100 |
| MDA-MB-435 | 0.85 | 3.86 | 1.77 | 8.43 | 1.91 | 9.23 | 2.01 | 12.0 |
| SK-MEL-5 | 2.31 | >50.0 | 3.47 | >50.0 | — | — | — | — |
| UACC-62 | 2.33 | >50.0 | 3.38 | 39.6 | — | — | — | — |
| Ovarian Cancer | | | | | | | | |
| OVCAR-3 | 1.26 | >50.0 | 2.77 | 33.1 | 2.46 | 46.2 | 2.38 | 20.9 |
| NCI/ADR-RES | 2.91 | >50.0 | 3.23 | >100 | 2.59 | >100 | 3.14 | >100 |
| Prostrate Cancer | | | | | | | | |
| DU-145 | 2.41 | >50.0 | 3.01 | 53.6 | — | — | — | — |
| UO-31 | — | — | — | — | 3.93 | >100 | 3.72 | >100 |

The N-4-methoxybenzoyl analog 3k exhibited good growth inhibition in all four leukemia cell lines in the panel, with $GI_{50}$ values in the range of 1.45-3.91 µM. Compound 3k exhibited potent growth inhibitory activity against SR leukemia ($GI_{50}$=1.45 µM; $LC_{50}$=39.4 µM), melanoma MDA-MB-435 ($GI_{50}$=850 nM; $LC_{50}$=3.86 µM) and LOX-IMVI ($GI_{50}$=1.86 µM; $LC_{50}$≥50 µM) cancer cell lines, and against ovarian OVCAR-3 ($GI_{50}$=1.26 µM; $LC_{50}$≥50 µM), colon cancer HCT-116 ($GI_{50}$=1.95 µM; $LC_{50}$≥50 µM), HCT-15 ($GI_{50}$=1.80 µM; $LC_{50}$≥50 µM), KM12 ($GI_{50}$=1.99 µM; $LC_{50}$≥50 µM) cell lines (Table 4).

The related N-2-bromobenzoyl compound 3s also exhibited growth inhibitory properties against all four leukemia cell lines in the panel ($GI_{50}$ values in the range of 2.55-4.00 µM). Compound 3s also showed good growth inhibitory activity against melanoma MDA-MB-435 cell lines ($GI_{50}$=1.77 µM; $LC_{50}$=8.43 µM) (Table 4).

The N-1-naphthoyl analog 3t exhibited growth inhibitory properties against all four leukemia cancer cell lines in the panel ($GI_{50}$ values in the range of 2.74-3.71 µM). Compound 3t also showed good growth inhibitory activity against HOP-92 non-small cell lung cancer ($GI_{50}$=1.30 µM; $LC_{50}$=44.8 µM), and MDA-MB-435 melanoma ($GI_{50}$=1.91 µM; $LC_{50}$=9.23 µM) cell lines (Table 4).

The N-1-naphthoyl analog 3w, which differs from 3t in possessing an indolic 5-methoxy group exhibited good growth inhibition in all four leukemia cancer cell lines in the panel ($GI_{50}$ values in the range of 3.31-3.95 µM), and in the three melanoma cell lines ($GI_{50}$ values in the range of 1.91-3.80 µM), and also showed potent growth inhibitory activity against HOP-92 non-small cell lung cancer ($GI_{50}$=1.09 µM; $LC_{50}$≥100 µM) and OVCAR-3 ovarian cancer cells ($GI_{50}$ and $LC_{50}$ values of 2.38 µM and 20.9 µM, respectively) (Table 4). The isomeric N-2-naphthoyl analogs of 3t and 3w (3x and 3z, respectively) were not identified as potent cytotoxic agents against any of the human cancer cell lines in the 60 cell panel.

Example 3

Based on recent modeling studies on the structurally related 5-((1-aroyl-1H-indol-3-yl)methylene)-2-oxodihydropyrimidine-4,6(1H,5H)-diones, molecular docking studies were performed with the two active molecules 3k and 3w at the active site of COX-2 with PDB ID: 6COX. The Fred 2.2.5 program from Openeye scientific software was used as the docking tool in this disclosure. The built-in Chemscore score was selected as the optimization filter and consensus score for the final selection of docking poses. The active site comprised all the atoms within 8 Å of the co-crystallized ligand. After validation, molecular docking was performed on the two active compounds (3k and 3w). The molecular docking experiment was validated using the standard re-docking procedure. Re-docking of the existing ligand, Sc-558, into its binding site resulted in <1.5 Å root mean square distance (RMSD) between the co-crystallized ligand and the docked ligand.

The carbonyl and amine groups on the barbiturate moiety in analogs related to scaffold B (FIG. 1) are involved in hydrogen bonding interactions with residues SER353, GLN192, and HIS90. Without being bound by theory, the thiobarbiturate moiety may occupy the pocket formed by residues TYR385, VAL523, TRP387, and SER530. The binding mode proposed in this study seems to be more reliable than any previously reported model, mainly due to the more favorable interactions that the thiobarbiturate moiety makes with the surrounding residues (TYR385, VAL523, TRP387, and SER530). The docking of compound 3k and 3w into the active site is displayed in FIGS. 2 and 3, respectively.

Figure 2:
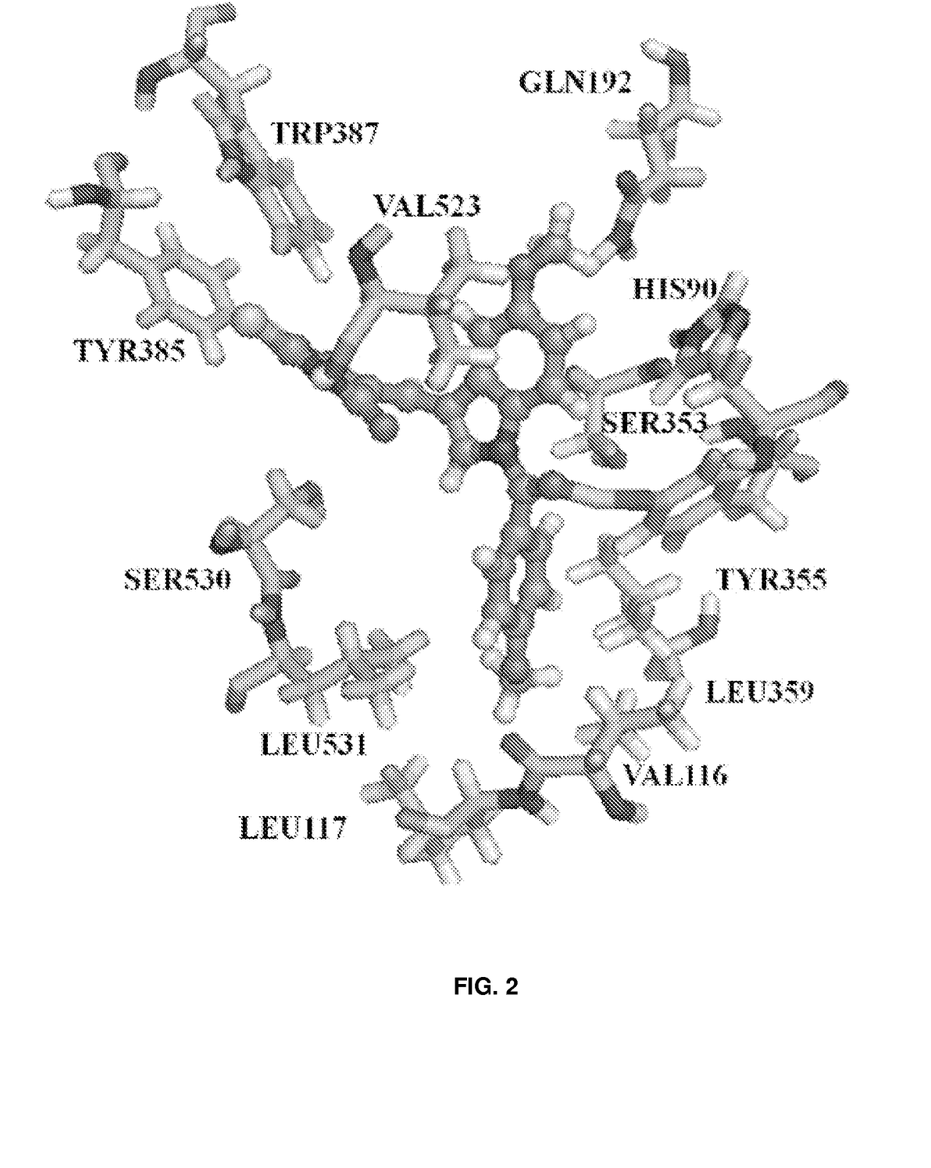
FIG. 2 illustrates compound 3k binding at the active site of COX-2. Compound 3k is displayed as a ball-and-stick model at the center, and the active site residues are displayed as a stick model around the periphery.

As shown in FIG. 2, the ligand is strongly stabilized by both polar and non-polar interactions. The indolic moiety in the molecule acts as an anchor, holding the ligand in position by strong hydrophobic interactions with multiple residues at the active site; i.e., SER353 and VAL523. The 2-thiobarbituric acid group is stabilized by hydrogen bonding interactions with the side chain of TYR385, hydrogen bonding with the backbone of VAL523, hydrophobic interactions with TRP387, and CH-π interactions with SER530 residues. The indolic methoxy group is strongly stabilized by hydrogen bonding to GLN192 and the phenyl ring of the indole moiety by van der Waals interactions with HIS90 and Val523.

Figure 3:
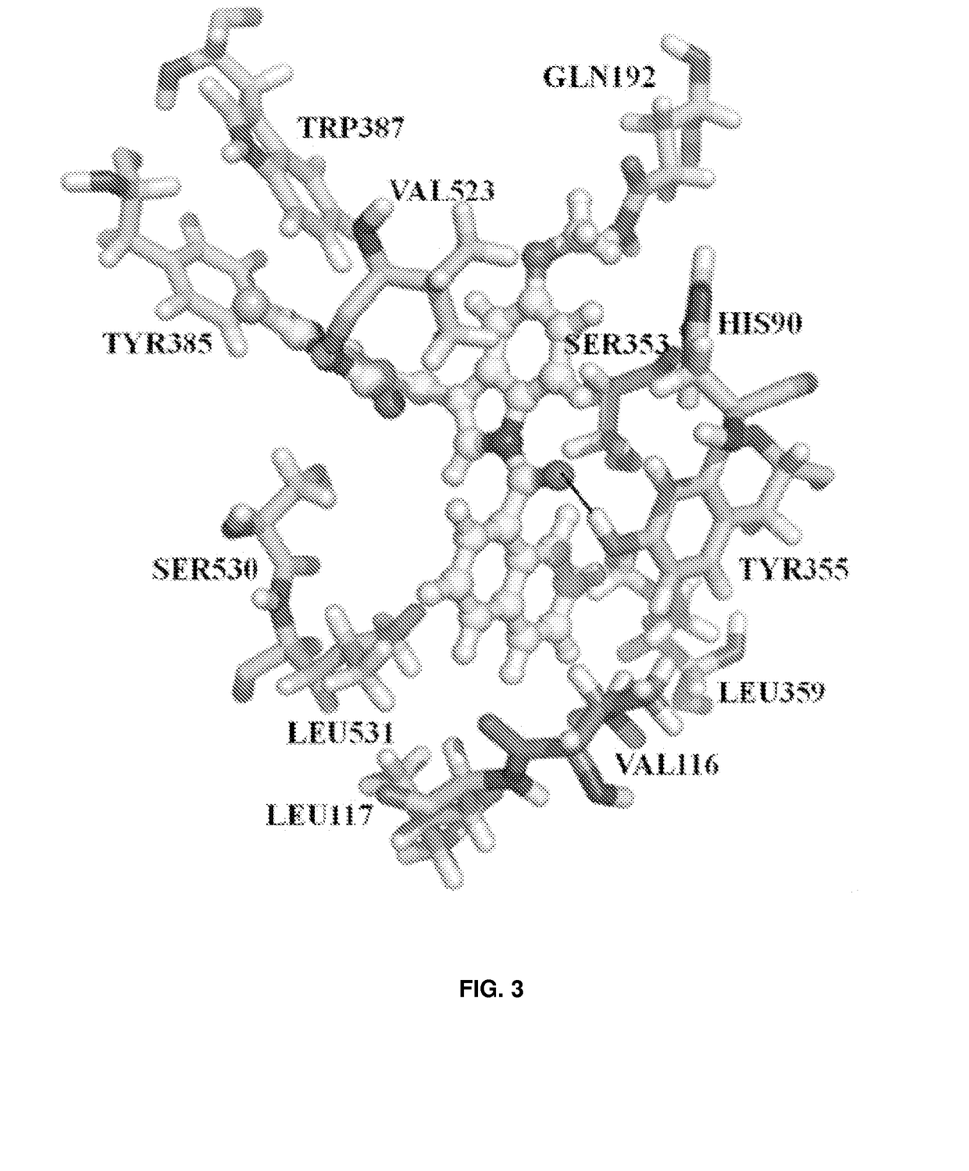
FIG. 3 illustrates compound 3w binding at the active site of COX-2. Compound 3w is displayed as a ball-and-stick model at the center, and the active site residues are displayed as a stick model around the periphery.

Compound 3w differs from 3k by replacement of the N-4-methoxybenzoyl group in 3k with an N-1-naphthoyl group. Nevertheless, both compounds are bound in a similar orientation at the active site of COX-2. The N-1-naphthoyl moiety occupies the hydrophobic pocket formed by TYR355, LEU359, LEU531, VAL116, and LEU117; moreover, the non-polar N-1-naphthoylmoiety is an ideal group for occupying this hydrophobic pocket. The binding of 3w at the active site of COX-2 is shown in FIG. 3.

Figure 4:
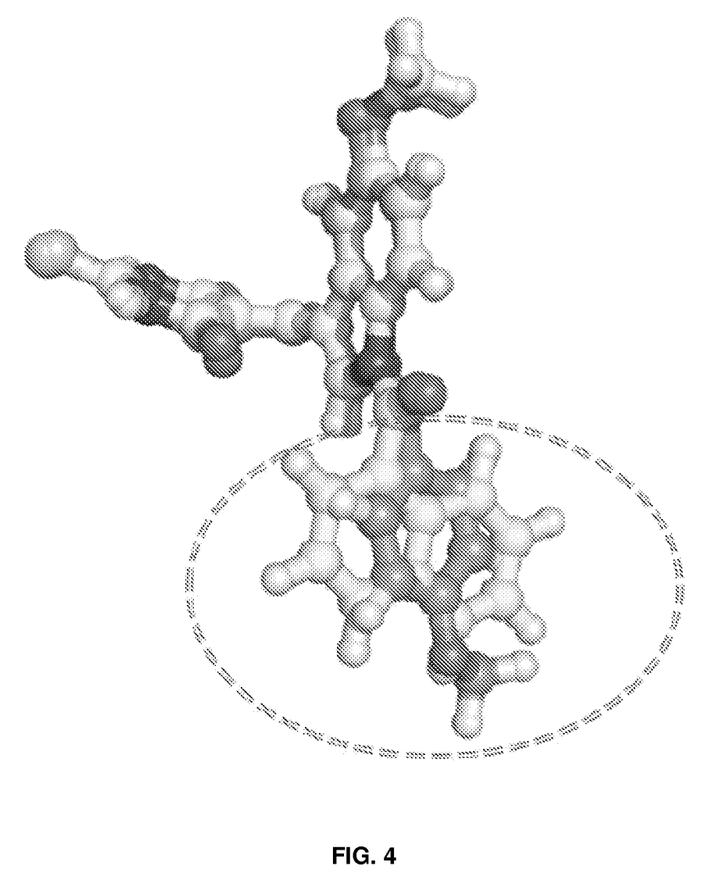
FIG. 4 illustrates the superimposition of binding modes of compounds 3k and 3w. A close alignment of the carbon chain of both compounds is demonstrated. Highlighted in the circle is the difference between the two compounds.

The superimposition of both compounds at the COX-2 active is further shown in FIG. 4. Thus, the binding of these compounds with strong hydrophobic and hydrogen bonding interactions at the active site of COX-2 indicates high affinity for COX-2 ligands. Furthermore, the new binding modes proposed herein further reveal that compound 3w binds in a similar orientation and conformation as compound 3k at the active site of COX-2 (FIG. 4).

What is claimed is:

1. A compound comprising Formula (I) or a pharmaceutically acceptable salt thereof:

(I)

wherein:
$R^1$ is chosen from hydrogen, halogen, hydrocarbyl, and substituted hydrocarbyl;
$R^2$ is chosen from hydrocarbyl and substituted hydrocarbyl;
$X^1$ is chosen from hydrocarbyl, substituted hydrocarbyl, nitrogen, oxygen, and sulfur;
$X^2$ is chosen from hydrocarbyl, substituted hydrocarbyl, nitrogen, oxygen, and sulfur; and
n is an integer from 0 to 10.

2. The compound of claim 1, wherein n is 0, 1, or 2.

3. The compound of claim 1, wherein one of $X^1$ and $X^2$ is nitrogen.

4. The compound of claim 1, wherein $X^1$ and $X^2$ are both nitrogen.

5. The compound of claim 1, wherein $R^1$ is hydrogen.

6. The compound of claim 1, wherein $R^1$ is halogen.

7. The compound of claim 6, wherein $R^1$ is bromo or chloro.

8. The compound of claim 1, wherein $R^1$ is $OCH_3$.

9. The compound of claim 1, wherein $R^2$ is hydrocarbyl selected from the group consisting of phenyl, 1-naphthyl, and 2-naphthyl.

10. The compound of claim 1, wherein $R^2$ is substituted hydrocarbyl selected from the group consisting of 4-F—$C_6H_4$, 4-$OCH_3$—$C_6H_4$, 4-CN—$C_6H_4$, 4-$COOCH_3$—$C_6H_4$, and 2-Br—$C_6H_4$.

11. A compound comprising Formula (II) or a pharmaceutically acceptable salt thereof:

(II)

wherein:
$R^1$ is chosen from hydrogen, halogen, hydrocarbyl, and substituted hydrocarbyl;
$R^2$ is chosen from hydrocarbyl, and substituted hydrocarbyl; and
n is an integer from 0 to 10.

12. The compound of claim 11, wherein $R^1$ is hydrogen.

13. The compound of claim 11, wherein $R^1$ is halogen.

14. The compound of claim 13, wherein $R^1$ is bromo or chloro.

15. The compound of claim 11, wherein $R^1$ is $OCH_3$.

16. The compound of claim 11, wherein $R^2$ is hydrocarbyl selected from the group consisting of phenyl, 1-naphthyl, and 2-naphthyl.

17. The compound of claim 11, wherein $R^2$ is substituted hydrocarbyl selected from the group consisting of 4-F—$C_6H_4$, 4-$OCH_3$—$C_6H_4$, 4-CN—$C_6H_4$, 4-$COOCH_3$—$C_6H_4$, and 2-Br—$C_6H_4$.

18. A pharmaceutical composition comprising a pharmaceutically acceptable excipient and a compound of claim 1.

19. A combination comprising an anti-inflammatory agent and/or a chemotherapeutic agent, and a compound of claim 1.

20. A method for treating inflammation, treating an inflammation related disorder, inhibiting COX-2, treating cancer, reducing the size of a neoplasm, or inhibiting tubulin polymerization in a cell of a subject in need thereof, the method comprising administering to the subject a compound of claim 1.

* * * * *